United States Patent
Bermak et al.

(10) Patent No.: US 11,910,851 B2
(45) Date of Patent: Feb. 27, 2024

(54) SMART MASK WITH PRINTED ELECTRONICS

(71) Applicant: Qatar Foundation for Education, Science and Community Development, Doha (QA)

(72) Inventors: Amine Bermak, Doha (QA); Saleem Khan, Doha (QA); Shawkat Ali, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 783 days.

(21) Appl. No.: 17/036,936

(22) Filed: Sep. 29, 2020

(65) Prior Publication Data

US 2022/0047009 A1 Feb. 17, 2022

(51) Int. Cl.
| | |
|---|---|
| A41D 13/00 | (2006.01) |
| A41D 13/11 | (2006.01) |
| A61B 5/0205 | (2006.01) |
| A41D 1/00 | (2018.01) |

(52) U.S. Cl.
CPC .............. *A41D 13/11* (2013.01); *A41D 1/002* (2013.01); *A61B 5/02055* (2013.01)

(58) Field of Classification Search
CPC ..... A41D 13/11; A41D 1/002; A61B 5/02055
See application file for complete search history.

(56) References Cited

U.S. PATENT DOCUMENTS

| | | | |
|---|---|---|---|
| 9,943,252 B1 | 4/2018 | Kayyali | |
| 2019/0254538 A1* | 8/2019 | Erdman | A61B 5/6803 |
| 2020/0397087 A1* | 12/2020 | Crenshaw | A41D 1/002 |
| 2021/0093205 A1* | 4/2021 | Zhao | A61B 5/6803 |
| 2021/0330259 A1* | 10/2021 | Liu | A61B 5/14552 |
| 2022/0071562 A1* | 3/2022 | Kiani | A62B 18/08 |
| 2022/0096874 A1* | 3/2022 | Connor | A62B 18/025 |
| 2022/0266068 A1* | 8/2022 | Connor | A62B 7/10 |

FOREIGN PATENT DOCUMENTS

| | | |
|---|---|---|
| CN | 104814544 A | 8/2015 |
| CN | 107405508 A | 11/2017 |
| WO | 2015166444 A1 | 11/2015 |
| WO | 2016200109 A1 | 12/2016 |
| WO | 2020092701 A2 | 5/2020 |

* cited by examiner

*Primary Examiner* — Steven O Douglas
(74) *Attorney, Agent, or Firm* — K&L Gates LLP

(57) ABSTRACT

A facial mask configured to be worn by a user includes a mask substrate, a temperature and respiration rate sensor for monitoring the temperature and breathing rate of the user, a humidity sensor for monitoring the humidity of the breath of the user, and a cough sensor for monitoring the cough rate of the user. The sensors may be printed onto a sensor array substrate, which is then secured to the mask substrate. The sensors provide real-time monitoring of the temperature, the breathing rate, the humidity, and the cough rate of the user.

11 Claims, 4 Drawing Sheets

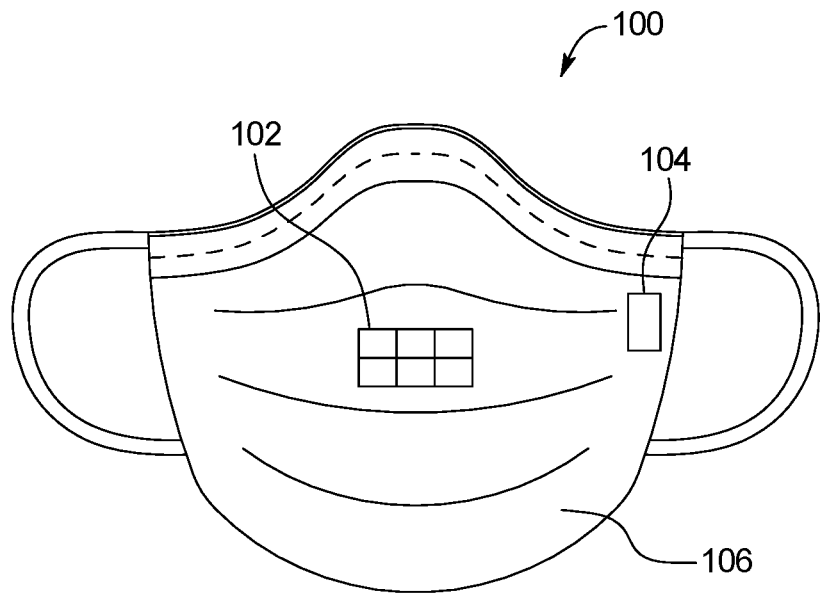
FIG. 1
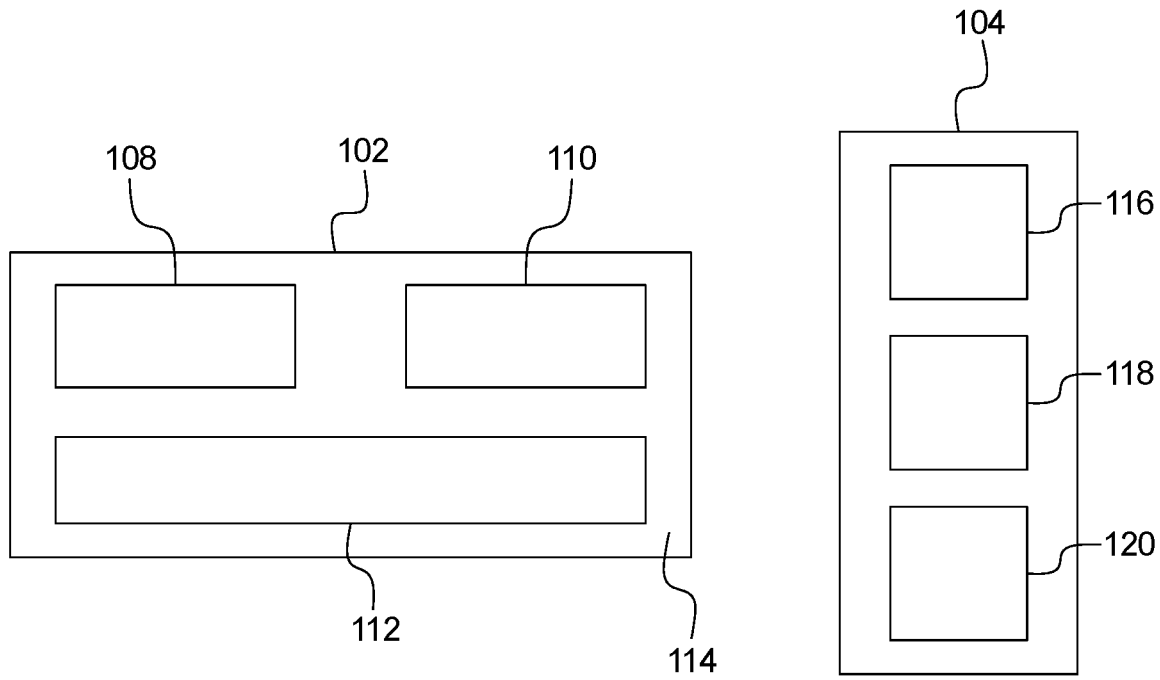
FIG. 2A
FIG. 2B

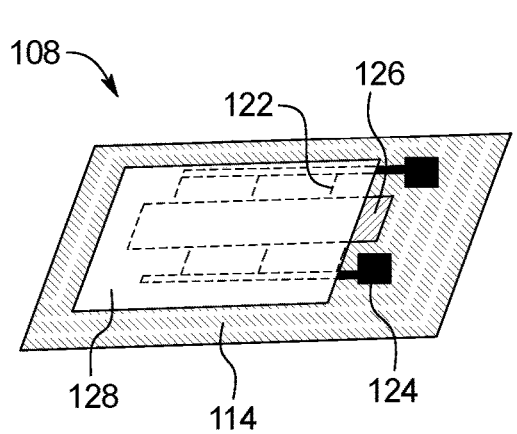
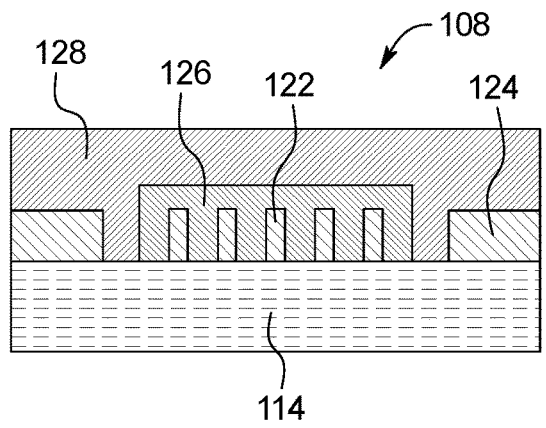
FIG. 3A
FIG. 3B
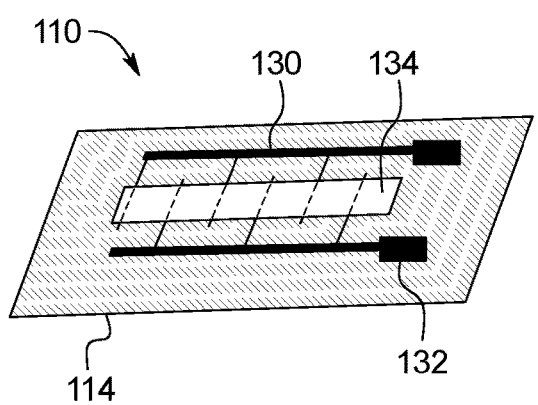
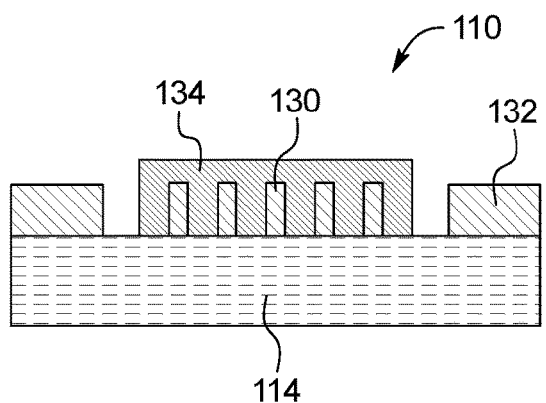
FIG. 4A
FIG. 4B
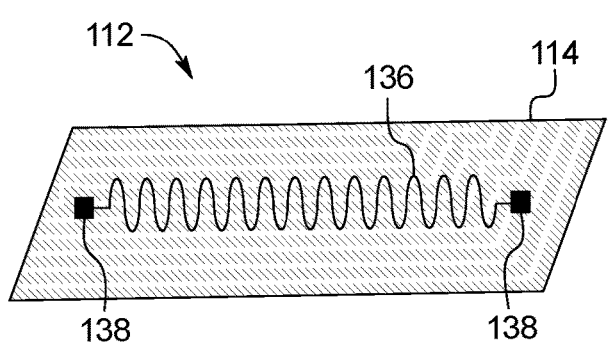
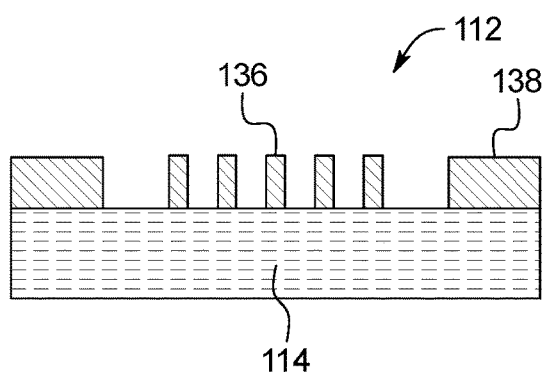
FIG. 5A
FIG. 5B

SMART MASK WITH PRINTED ELECTRONICS

CROSS-REFERENCE TO RELATED APPLICATIONS

Pursuant to 35 U.S.C. § 119(a), this application claims the benefit of earlier filing date and right of priority to Qatar Application No. QA/202008/00425, filed on Aug. 11, 2020, the contents of which are incorporated by reference herein in its entirety.

BACKGROUND

The present invention relates to the development of a smart mask equipped with printed sensors for real-time monitoring of human health conditions, especially flu-like symptoms.

Infectious diseases are transmitted between people in close proximity through airborne droplets. Airborne droplets carrying the disease from an infected person to others are transmitted through coughing, sneezing, talking, or heavy breathing. Wearing a facial covering or mask when interacting with others minimizes the spread of infection and has become commonplace in many areas given the recent rise of COVID-19.

The status of a person's health with respect to infectious diseases can be monitored through certain biomarkers. Compared to the various on-body mounted wearable sensing devices, the presence of potential biomarkers in human exhaled breath is a prime alternative for diagnosing several chronic diseases. Particularly in the case of flu-like diseases such as COVID-19 and pneumonia, higher body temperature, irregular breathing rate, and continuous coughing are early prominent symptoms of these diseases.

Accordingly, there is a need for a wearable facial mask that allows for the monitoring of biomarkers.

SUMMARY

A smart, wearable facial mask is used to monitor the various biomarkers including breathing rate, cough, humidity, and temperature levels in human breathing. The smart mask as described herein allows for early detection of infectious diseases through monitoring of higher body temperature, irregular breathing rate, and continuous coughing, which are early prominent symptoms of these diseases.

Monitoring the breathing rate is critical for subjects with irregularities in breath cycles causing serious health implications. Similarly, deep body temperature is a quick biomarker for rapid detection of various viral, cancerous, and lung infectious diseases. Coughing is monitored through a pressure sensor and correlated with data from a humidity sensor to determine the dryness of the cough. The combination of these various, cost-effective sensors printed onto a single patch and secured onto a facial mask will help in rapid detection of the vital signs. Use of the smart mask described herein also allows for real-time and continuous monitoring around the clock, helping to keep track of patients during quarantine periods as well as in normal routine life. Continuous monitoring will reduce the burden of medical experts attending to the patients.

In one embodiment, the smart mask includes a sensor array and a wireless communication module secured to a mask substrate. The sensor array or patch includes a temperature and respiration rate sensor, a humidity sensor, and a cough detection sensor positioned or printed on a sensor array substrate, which is secured to the mask substrate. Data collected from the sensors is transmitted to the wireless communication module, which in turn transmits the data to the user's mobile phone, a further device, or remote storage.

The sensor array may be developed as a single patch and placed on the facial mask substrate in such a way that the human breath is directed to cover the full surface area of the sensor array. Data collected from the sensors is processed and transmitted through a Bluetooth device within the wireless communication module to a smart phone of the user or other device.

The temperature and respiration rate sensor includes an electrode printed onto the sensor array substrate and a sensing film extending across the arms of the electrode. An encapsulant layer protects the electrode and the sensing film. During the exhale cycle, the sensor detects a high temperature, which corresponds to the deep body temperature of the user. While, during inhale cycle, the sensor experiences a low temperature due to ambient airflow intake. This cycling of the high and low temperatures sensed by the sensor during the exhale and inhale cycles, respectively, determines the respiration rate of the user.

In one embodiment, nanomaterials-based metal interdigital electrodes (IDEs) of the temperature and breath sensor are printed onto the sensor array substrate and filled with the temperature-sensing layer. The interconnection and pads are also printed by using the same metallic ink for the readout. The encapsulant layer is applied on the whole sensing area using a screen printing technology. In other embodiments, the electrodes and connecting pads are secured to the sensor array substrate using other suitable methodologies.

The humidity sensor includes an electrode positioned atop the sensor array substrate and a sensing film extending across the arms of the electrode. The humidity sensor is composed of interdigital electrodes covered with a humidity sensing layer. Nanoparticles-based metallic ink is patterned using inkjet printing technology, and the spacing between the electrodes is filled with a nanocomposite material sensitive to minute variations in the humidity. The nanocomposite based thin film is highly sensitive with quick response and recovery time of 0.25 sec and 0.35 seconds, respectively, under standard temperature and pressure.

The cough sensor includes a sensing pattern comprised of a piezoresistive material having a repeated horse shoe shape on a stretchable substrate that allows for the impregnation of metal nanoparticles ink. A slight variation in force on the fabric caused by coughing is used to detect the rate, intensity, and condition (dry or humid) of the cough. Upon the force application via coughing on the fabric, the resistance within the sensing pattern decreases due to the shrinkage of conducting threads, and resets to the initial resistance when released. The relationship between the sensing performance of the woven fabric and its 3D network structure is established by the yarn shrinkage and arrangement density. The resistance modulation phenomenon corresponds to the cough detection and sensing applications.

The sensor array is interconnected to a signal conditioning circuit on the sensor array substrate to eliminate the redundant data generated through the exposure of the sensors to the surrounding environment. The conditioning circuits are connected to a low power wireless transmission module on the wireless communication system, which sends the sensors' data to the mobile phone of the user. The wireless communication system is printed onto a detachable module, which is connected to the connecting pads of each corresponding sensor through flexible zip connectors.

An object of the invention is to monitor biomarkers for early detection of infectious diseases.

A further object of the invention is to monitor biomarkers over an extended period of time.

Another object of the invention is to utilize inkjet technology to produce a smart face mask at a low cost.

Additional objects, advantages, and novel features of the examples will be set forth in part in the description which follows, and in part will become apparent to those skilled in the art upon examination of the following description and accompanying drawings or may be learned by production or operation of the examples. The objects and advantages of the concepts may be realized and attained by means of the methodologies, instrumentalities, and combinations particularly pointed out in the appended claims.

BRIEF DESCRIPTION OF THE DRAWINGS

The drawing figures depict one or more implementations in accordance with the present concepts, by way of example only, not by way of limitations. In the figures, like reference numerals refer to the same or similar elements.

FIG. 1 is a block diagram of a smart facial mask as disclosed in the present application.

FIGS. 2A and 2B are block diagram plan views of the sensors array and wireless communication system of the smart mask of FIG. 1.

FIGS. 3A and 3B are schematic plan and cross-sectional diagrams of the temperature/breathe rate sensor of the smart mask of FIG. 1.

FIGS. 4A and 4B are schematic plan and cross sectional diagrams of the humidity sensor of the smart mask of FIG. 1.

FIGS. 5A and 5B are schematic plan and cross sectional diagrams of the cough detection sensor of the smart mask of FIG. 1.

DETAILED DESCRIPTION

Figure 6:
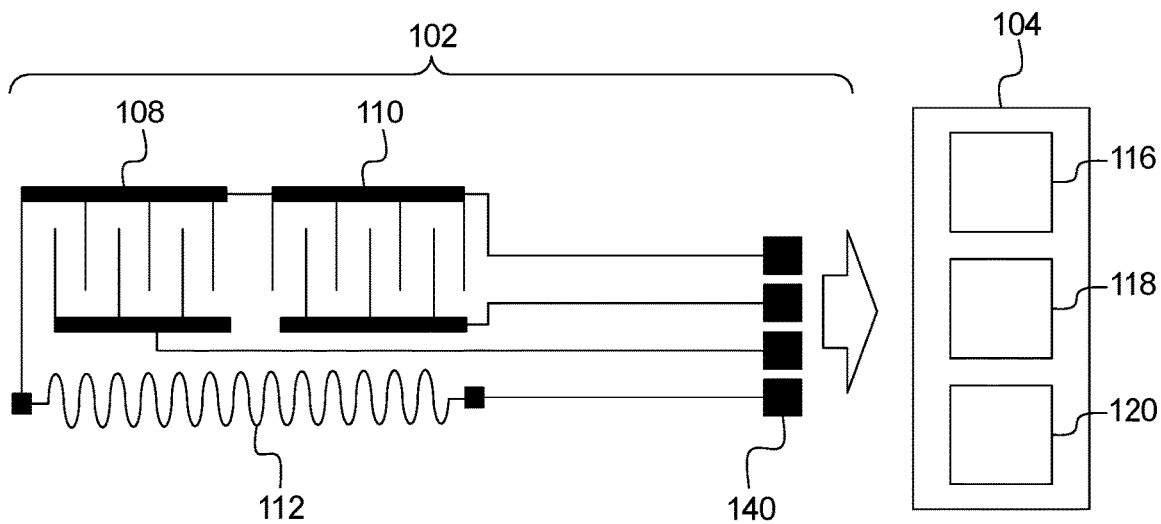
FIG. 6 is a schematic diagram of the sensor array interfacing with a communication module of the smart mask of FIG. 1.

FIG. 1 illustrates a smart facial mask 100 of the present application. The mask 100 includes a sensor array 102 and a wireless communication system 104 that are secured to a mask substrate 106 and that allow for collecting and monitoring of biomarker data related to human vital signs, such as deep body temperature, respiration rate, breathe humidity, and cough detection, for early detection of various diseases.

As shown in FIG. 2A, the sensor array 102 includes a temperature and respiration rate sensor 108, a humidity sensor 110, and a cough detection sensor 112 on a sensor array substrate 114. The wireless communication system 104 includes a power management and charging unit 116, a microcontroller 118, and a Bluetooth unit 120 as shown in FIG. 2B.

In a preferred embodiment, the sensor array 102 is developed using a low-cost inkjet printing technology onto a thermally transferable substrate, such as polymeric-based substrates. A transfer printing process may be used to integrate the sensor array into the smart mask. More specifically, the sensor array 102 is printed onto a secondary substrate as described in greater detail below, which is then embedded on the smart mask. In one embodiment, the sensor array substrate 114 may comprise a cotton fabric material or any suitable material. The sensor array 102 may include additional sensors for monitoring of other biomarkers such as volatile organic compounds (VOCs) present in the user's breath.

A schematic diagram of the temperature/breathe rate sensor 108 is provided in FIGS. 3A and 3B. Silver interdigital electrodes 122 having connecting pads 124 are positioned atop the sensor array substrate 114, and a sensing film 126 extends across the arms of the electrodes 122. An encapsulation layer 128 protects the electrodes 122 and the sensing film 124. Referring to FIG. 3B, the cross-sectional view of the sensor 108 shows the substrate 114, the interdigital electrodes 122, the sensing film 124, the connecting pads 126, and the encapsulation layer 128.

Temperature and breathe rate sensors are combined into a single sensor 108 that monitors the deep body temperature and respiration rate. During the exhale cycle, the sensor 108 detects a high temperature, which corresponds to the deep body temperature of the user. While, during the inhale cycle, the sensor 108 experiences a low temperature due to ambient airflow intake. The temperature sensor 108 therefore experiences high and low temperatures during the exhale and inhale cycles, respectively, of breathing. This cycling of the instantons temperature of the temperature sensor determines the respiration rate of the user.

According to the one or more embodiments, the temperature and breath sensor 108 is produced by printing nanomaterials-based metal interdigital electrodes (IDEs) 122 and filled with the temperature-sensing layer 126. An equal spacing between the electrodes is maintained to ensure containment of the sensing layer 126 and exposure to a detection event without being interrupted by the surrounding environment. The interconnection and pads 124 are also printed by using the same metallic ink for the readout. A thin encapsulation layer 128 is applied on the sensing layer 126 as well as on the metal electrodes 122 in order to reduce the likelihood of oxidation on the metal electrodes 122 and the exposure of the temperature sensing layer 126 to humidity. The encapsulant layer 128 is applied on the entirety of the sensing area using a screen printing technology.

FIGS. 4A and 4B illustrate schematic diagrams of the humidity sensor 110 including interdigital electrodes 130, connecting pads 132, and a sensing film 134 on the sensor array substrate 114.

According to another embodiment, the humidity sensor 110 printed on the sensor array substrate 114 is composed of interdigital electrodes 130 covered with humidity sensing layer 134. Nanoparticles based metallic ink is patterned using inkjet printing technology, whereas the spacing between the electrodes 130 is filled with a nanocomposite material sensitive to minute variations in the humidity. The nanocomposite based thin film is highly sensitive with quick response and recovery time of 0.25 sec and 0.35 seconds, respectively, under standard temperature and pressure. This high speed and less recovery time are ideal for the monitoring the humidity level of a human breath, which changes in each cycle of the exhale and inhale. The printed sensor 110 is highly sensitive of about 96.36% in detectable range from 5% to 95% RH, which has negligible cross sensitivity from other constituents in air due to the distinguished properties of the nanocomposite layer. The interaction of OH− molecules with the nanocomposite is highly detectable as the electrical resistance of the sensor goes down by completing the current paths with OH− molecules.

FIGS. 5A and 5B show schematic diagrams of the cough detection sensor 112. The sensor 112 includes a sensing pattern 136 and connecting pads 138 on the sensor array substrate 114. The sensing pattern 136 may be comprised of a piezoresistive material or other suitable material. While a horse-shoe pattern in shown in FIG. 5A, other patterns may be used as desired.

The cough sensor 112 is printed for measuring the coughing rate of the user. The cough sensor 112 is patterned in a horse-shoe shape as shown in FIG. 5A using a stretchable substrate (cotton fabric) that allows impregnation with the metal nanoparticles ink. The sensor 112 works similar to a strain sensor, where the change in electrical resistance corresponds to a detection of force application. The slight variation due to the instantaneous pressure applied as a result of coughing is used to detect the rate, intensity, and condition (dry or humid) of the cough. Upon the force application via coughing on the fabric, the resistance decreases due to the shrinkage of conducting threads, and resets to the initial resistance when released. The relationship between the sensing performance of the woven fabric and the 3D network structure is established by the yarn shrinkage and arrangement density. The resistance modulation phenomenon corresponds to the cough detection and sensing applications.

FIG. 6 illustrates the overall sensor array 102 as it interfaces with the communication module 104. The communication module 104 includes a power management and charging unit 116, a microcontroller 118 for the signal conditioning and processing, and a low power Bluetooth unit 120. All sensors 108, 110, 112 are connected to connecting pads 140, which in turn connect with the microcontroller 118, which processes data from the sensors 108, 110, 112 in real-time and then transmits the data using the Bluetooth unit 120. In other embodiments, an alternative wireless technology may be used instead of Bluetooth.

The wireless communication system 104 is printed onto a detachable substrate, which is connected to the connecting pads of each corresponding sensor through flexible zip connectors. The detachable substrate is attached to a side of the smart mask 100 to minimize interference with the data collected by the sensors 108, 110, 112 as well as to avoid obstructions to the natural breathing and respiration. The detachable communication module 104 offers an opportunity to replace the communication module 104 or disconnect the module 104 for charging the power battery. The portable nature of the communication module 104 and the fast processing of the data with minimal interruption from the ambient environment present a more interesting and valuable contribution in development of this real-time health monitoring system.

Figure 7:
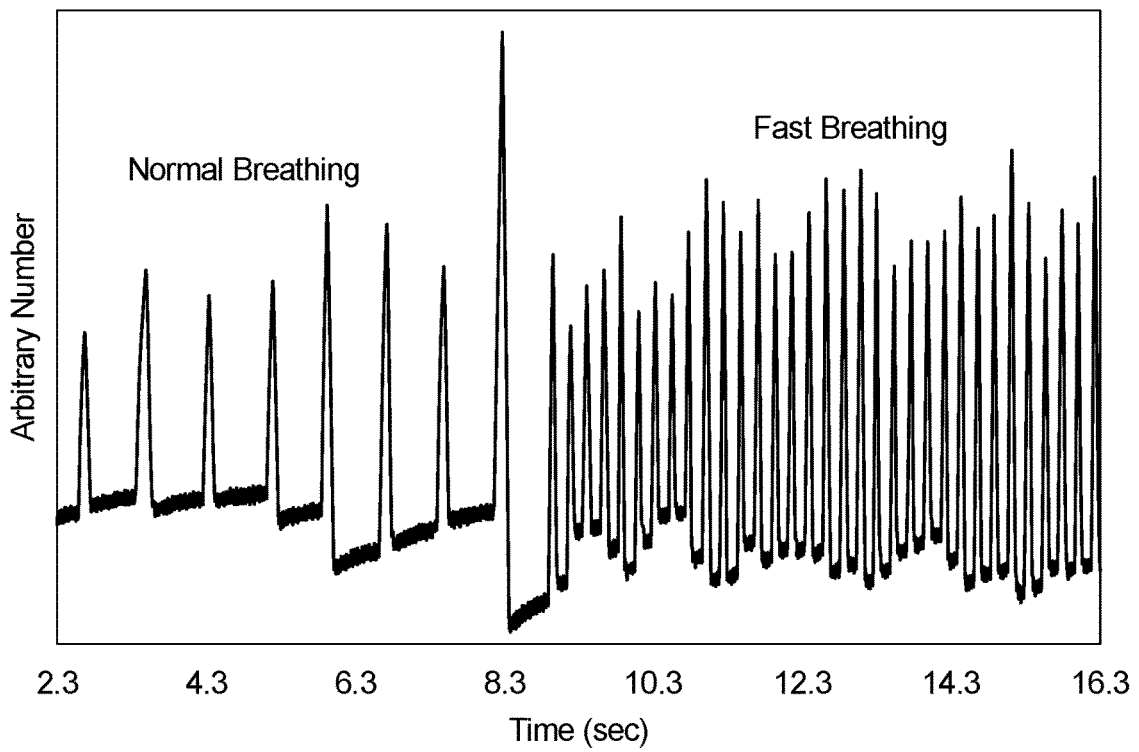
FIG. 7 illustrates experimental results of normal and fast breathing cycles in an embodiment of the smart mask of FIG. 1.

FIG. 7 provides experimental data of the normal and fast breathing cycles recorded by connecting the sensor 108 to a source meter and recording real-time data. The temperature and respiration rate sensor 108 allows for monitoring of breath temperature to allow for analysis of deep body temperature in addition to instantaneous data recording. The sensor 108 is used for breath monitoring as the temperature varies significantly during the inhale and exhale cycle. This data is very important for patients dealing with various chronic diseases and continuous monitoring of the health condition gives a deeper insight into the health condition leading medical experts to more valuable analysis and conclusions.

Figure 8:
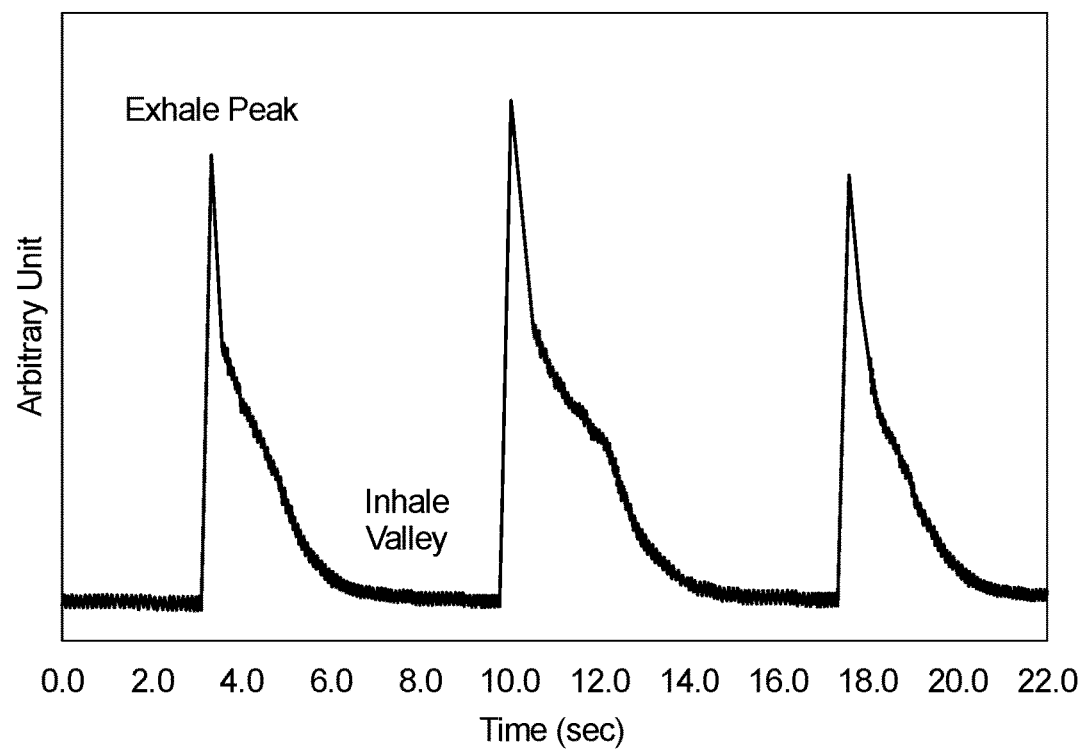
FIG. 8 illustrates experimental results showing humidity variation against inhale and exhale cycles in an embodiment of the smart mask of FIG. 1.

FIG. 8 provides details of the experimental results of the humidity levels, where the highest peak represents the exhale and the valley determines the inhale cycle of a human breath in real-time. Dry or hydrated conditions during both respiration and coughing are important biomarkers for various flu-like diseases and play a significant role in early detection of the disease. The prolonged monitoring provided by the smart mask 100 enables users to track the pattern of the symptoms and further developments.

Figure 9:
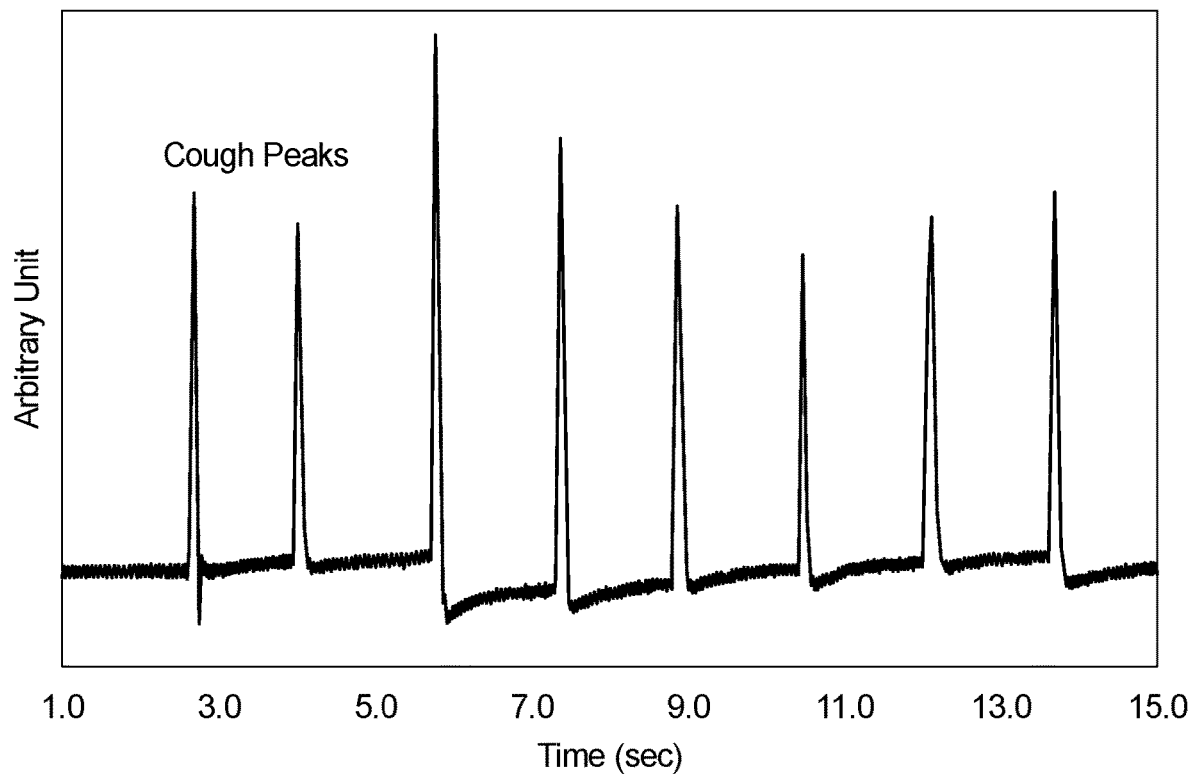
FIG. 9 illustrates experimental results of coughing peaks in an embodiment of the smart mask of FIG. 1.

FIG. 9 shows an experimental graph of the coughing peak, when the sensor 112 is subjected to strain caused by the coughing frequency. The real-time monitoring of coughing and the analysis of the dryness of the cough over long periods of time contributes significantly in discriminating the developed symptoms of the chronic diseases.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

We claim:

1. A facial mask configured to be worn by a user and to monitor breathing of the user, comprising:
    a mask substrate;
    a temperature and respiration rate sensor on the mask substrate for monitoring a temperature and a breathing rate of the user's breathing;
    a humidity sensor on the mask substrate for monitoring the humidity of the user's breathing; and
    a cough sensor on the mask substrate for monitoring the cough rate of the user's breathing,
    wherein each of the temperature and respiration rate sensor and the humidity sensor include an electrode, and wherein the electrode comprises a metallic ink that is printed onto a thermally sensitive sensor array substrate,
    wherein the temperature and respiration rate sensor, the humidity sensor, and the cough sensor provide real-time monitoring of the temperature, the breathing rate, the humidity, and the cough rate of the user.

2. The facial mask according to claim 1, wherein the cough sensor includes a piezoresistant material printed onto the thermally sensitive sensor array substrate.

3. The facial mask of claim 1, wherein the sensory array substrate is transfer printed onto the mask substrate.

4. The facial mask of claim 3, wherein the sensory array substrate is transfer printed onto the mask substrate through a thermal lamination process.

5. The facial mask according to claim 1, wherein the sensory array substrate is foldable and/or stretchable.

6. The facial mask according to claim 1, wherein data collected by the temperature and respiration rate sensor corresponds to a deep body temperature.

7. The facial mask according to claim 1, wherein data collected by the humidity sensor provides a dryness of the coughing.

8. The facial mask according to claim 1, wherein the cough sensor comprises a sensing pattern printed onto a flexible substrate that detects minute disturbances.

9. The facial mask according to claim 1, further comprising a lightweight signal conditioning circuit and a wireless transmission module for transmitting data collected by the sensors to a user device in real-time.

10. A facial mask configured to be worn by a user and to monitor breathing of the user, comprising:
 a mask substrate;
 a temperature and respiration rate sensor on the mask substrate for monitoring a temperature and a breathing rate of the user's breathing;
 a humidity sensor on the mask substrate for monitoring the humidity of the user's breathing; and
 a cough sensor on the mask substrate for monitoring the cough rate of the user's breathing, comprising a sensing pattern printed onto a flexible substrate that detects minute disturbances,
 wherein the temperature and respiration rate sensor, the humidity sensor, and the cough sensor provide real-time monitoring of the temperature, the breathing rate, the humidity, and the cough rate of the user.

11. A facial mask configured to be worn by a user and to monitor breathing of the user, comprising:
 a mask substrate;
 a temperature and respiration rate sensor on the mask substrate for monitoring a temperature and a breathing rate of the user's breathing;
 a humidity sensor on the mask substrate for monitoring the humidity of the user's breathing;
 a cough sensor on the mask substrate for monitoring the cough rate of the user's breathing; and
 a lightweight signal conditioning circuit and a wireless transmission module for transmitting data collected by the sensors to a user device in real-time,
 wherein the temperature and respiration rate sensor, the humidity sensor, and the cough sensor provide real-time monitoring of the temperature, the breathing rate, the humidity, and the cough rate of the user.

* * * * *